(12) United States Patent
Boyetchko et al.

(10) Patent No.: US 10,888,096 B2
(45) Date of Patent: Jan. 12, 2021

(54) BIOPESTICIDES FOR POTATO LATE BLIGHT DISEASE

(71) Applicant: Her Majesty the Queen in Right of Canada, as Represented By the Minister of Agriculture and Agri-Food, Saskatoon (CA)

(72) Inventors: Susan Boyetchko, Saskatoon (CA); Patrice Audy, Quebec (CA); Karen Sawchyn, Saskatoon (CA); Rejean Desgagnes, Quebec (CA); Ting Zhou, Guelph (CA); Tim Dumonceaux, Saskatoon (CA)

(73) Assignee: Her Majesty the Queen in Right of Canada, as Represented By the Minister of Agriculture and Agr, Saskatoon (CA)

( * ) Notice: Subject to any disclaimer, the term of this patent is extended or adjusted under 35 U.S.C. 154(b) by 52 days.

(21) Appl. No.: 16/077,400

(22) PCT Filed: Feb. 17, 2017

(86) PCT No.: PCT/CA2017/050157
§ 371 (c)(1),
(2) Date: Aug. 10, 2018

(87) PCT Pub. No.: WO2017/136944
PCT Pub. Date: Aug. 17, 2017

(65) Prior Publication Data
US 2019/0191708 A1 Jun. 27, 2019

Related U.S. Application Data

(60) Provisional application No. 62/294,068, filed on Feb. 11, 2016.

(51) Int. Cl.
*A01N 63/02* (2006.01)
*A01N 63/10* (2020.01)
*A01N 63/00* (2020.01)
*C12N 1/20* (2006.01)

(52) U.S. Cl.
CPC .............. *A01N 63/10* (2020.01); *A01N 63/00* (2013.01); *C12N 1/20* (2013.01)

(58) Field of Classification Search
CPC .................................. A01N 63/00; C12N 1/20
See application file for complete search history.

(56) References Cited

U.S. PATENT DOCUMENTS

2011/0077158 A1   3/2011   Slininger et al.

OTHER PUBLICATIONS

Partial Supplementary European Search Report dated Jul. 16, 2019, pp. 1-24.
A. Guyer et al.; "The Anti-Phytophthora Effect of Selected Potato-Associated Pseudomonas Strains: From the Laboratory to the Field"; Frontiers in Microbiology, Nov. 2015, vol. 6, Article 1309, pp. 1-13.
F. Daayf et al.; "Comparative screening of bacteria for biological control of potato late blight (strain US-8), using in-vitro, detached-leaves, and whole-plant testing systems"; Can. J. Plant Pathology. 25: 276-284 (2003).
International Search Report for PCT/CA2017/050157 dated May 4, 2017, pp. 1-6.
J. Hollywood; "Biological Control of Late Blight of Potatoes: in vivo and in vitro evaluation of microbial antagonists against tuber blight"; Thesis—Biology Department, University of London, published 2014, pp. 1-222.
J. Town et al.; "Genome Sequence of Pseudomonas chlororaphis Strain 189"; American Society for Microbiology; May/Jun. 2016, vol. 4, Issue 3, pp. 1-2.
J. Town et al.; "High-Quality Draft Genome Sequence of *Arthrobacter* sp. OY3WO11, a Strain That Inhibits the Growth of Phytophthora infestans"; American Society for Microbiology; May/Jun. 2016, vol. 4, Issue 3, pp. 1-2.
J. Town et al.; "High-Quality Draft Genome Sequence of Bacillus subtilis Strain WAUSV36"; American Society for Microbiology; May/Jun. 2016, vol. 4, Issue 3, pp. 1-2.
J. Town et al.; "High-Quality Draft Genome Sequence of Biocontrol Strain *Pantoea* sp. OXWO6B1"; American Society for Microbiology; May/Jun. 2016, vol. 4, Issue 3, pp. 1-2.
J. Town et al.; "Improved High-Quality Draft Genome Sequence of Pseudomonas fluorescens KENGFT3"; American Society for Microbiology; May/Jun. 2016, vol. 4, Issue 3, pp. 1-2.
N. Foran; "Bacterial antagonists as a biological solution for control of potato blight disease"; Thesis—McGill University, Montreal, Apr. 2016; pp. 1-89.
P.J. Slininger et al.; "Biological control of post-harvest late blight of potatoes"; Biocontrol Science and Technology, 2007; 17(5/6): 647-663.

*Primary Examiner* — Bin Shen
(74) *Attorney, Agent, or Firm* — Singleton Law, PLLC; Chainey P. Singleton

(57) ABSTRACT

Bacterial strains, or extracts thereof, are effective to control, treat or prevent infection of solanaceous plants with *Phytophthora infestans*, the causative agent of potato late blight disease. Also provided are biopesticidal formulations containing one or more of the bacterial strains or extracts thereof, and the use of the bacterial strains, extracts or biopesticidal formulations in the control, treatment and/or prevention of potato late blight disease.

24 Claims, 8 Drawing Sheets

Specification includes a Sequence Listing.

BIOPESTICIDES FOR POTATO LATE BLIGHT DISEASE

CROSS-REFERENCE TO RELATED APPLICATIONS

This application is a 371 of International Application No. PCT/CA2017/050157 filed on Feb. 17, 2017 which claims the benefit of U.S. Provisional Patent Application No. 62/294,068 filed Feb. 11, 2016.

BACKGROUND

The present application is directed to biopesticides for use in the treatment, control and/or prevention of potato late blight disease. More specifically, the present application is directed to bacterial strains which are useful in controlling the pathogen responsible for potato late blight disease.

Potato late blight disease, infamous for its implication in the Irish potato famine of the 1840s, is caused by infection of potato plants (*Solanum tuberosum* L.), and other solanaceous crops such as tomato and eggplant, by the pathogenic oomycete (water mold) *Phytophthora infestans* (Mont.) de Bary. The infection is characterized by black/brown lesions on the stems and leaves of the plant, which expand rapidly and become necrotic. Harvested afflicted potato tubers can decay upon storage or, if they survive the winter in storage or in the soil, can spread the disease to the next year's crop.

Current control measures involve an integrated pest management approach, including population monitoring of the pathogen, preventive measures such as crop rotation and sanitation (elimination or exclusion of infected plant parts from a farm), development of resistant crop varieties, and the use of chemical fungicides, which can require up to 12-15 applications per season, at a cost of millions of dollars. However, *Phytophthora infestans* is highly adaptive, and various new genotypes have developed resistance to the major fungicides, including metalaxyl and mefenoxam, or the ability to overcome resistance in crops. Thus, potato late blight disease is an ongoing problem and the world's most economically significant potato and tomato disease, contributing to an estimated global annual cost of over $6.7 billion for crop losses and other control measures.

Biopesticides, which are formulations containing naturally-occurring microorganisms that kill, suppress or reduce the vigor of a target pest, are a desirable alternative to chemical pesticides and other pest control mechanisms. Such biopesticides typically show lower human and mammalian toxicity, do not survive outside of their natural host or persist in the environment, and are generally regarded as safe. The microorganism component of a biopesticide is usually a bacterium, fungus or virus in a form which can propagate and infect the target pest, once applied. The microorganism can be host-specific to a particular species of pest, or have broad spectrum activity against a range of pest species. Mass production of such microorganisms using large-scale fermentation technology has contributed to the commercial viability of biopesticide production and use.

Therefore, microorganisms and biopesticidal formulations thereof which can be used to control potato late blight disease are desirable.

SUMMARY

In one aspect, the present invention provides a bacterial culture effective to control, treat or prevent potato late blight disease in plants. In at least one embodiment, the bacterial culture comprises one or more bacteria selected from *Pseudomonas chlororaphis* strain 189, *Bacillus subtilis* strain WAUSV36, *Pseudomonas fluorescens* strain UWO1, *Pseudomonas fluorescens* strain KENGFT3, *Arthrobacter* sp. strain OY3WO11 and *Pantoea* sp. strain OXWO6B1.

Another aspect of the present invention provides an extract from a bacterial culture as described herein, wherein the extract is effective to control, treat or prevent potato late blight disease in plants.

In another aspect, the present invention provides a biopesticidal formulation which is effective to control, treat or prevent potato late blight disease in plants comprising a bacterial culture as described herein, or an extract thereof, and a carrier.

A further aspect of the present invention provides the use of a bacterial culture or a biopesticidal formulation as described herein for control, treatment and/or prevention of potato late blight disease in plants.

Yet another aspect of the present invention provides a method of controlling, treating or preventing potato late blight disease in plants, the method including applying a bacterial culture as described herein, or an extract thereof, or a biopesticidal formulation thereof, to a plant, or part thereof, infected by, or at risk of infection by, *Phytophthora infestans*.

BRIEF DESCRIPTION OF THE DRAWINGS

Further features of the present invention will become apparent from the following written description and the accompanying figures, in which.

DETAILED DESCRIPTION

Figure 1:
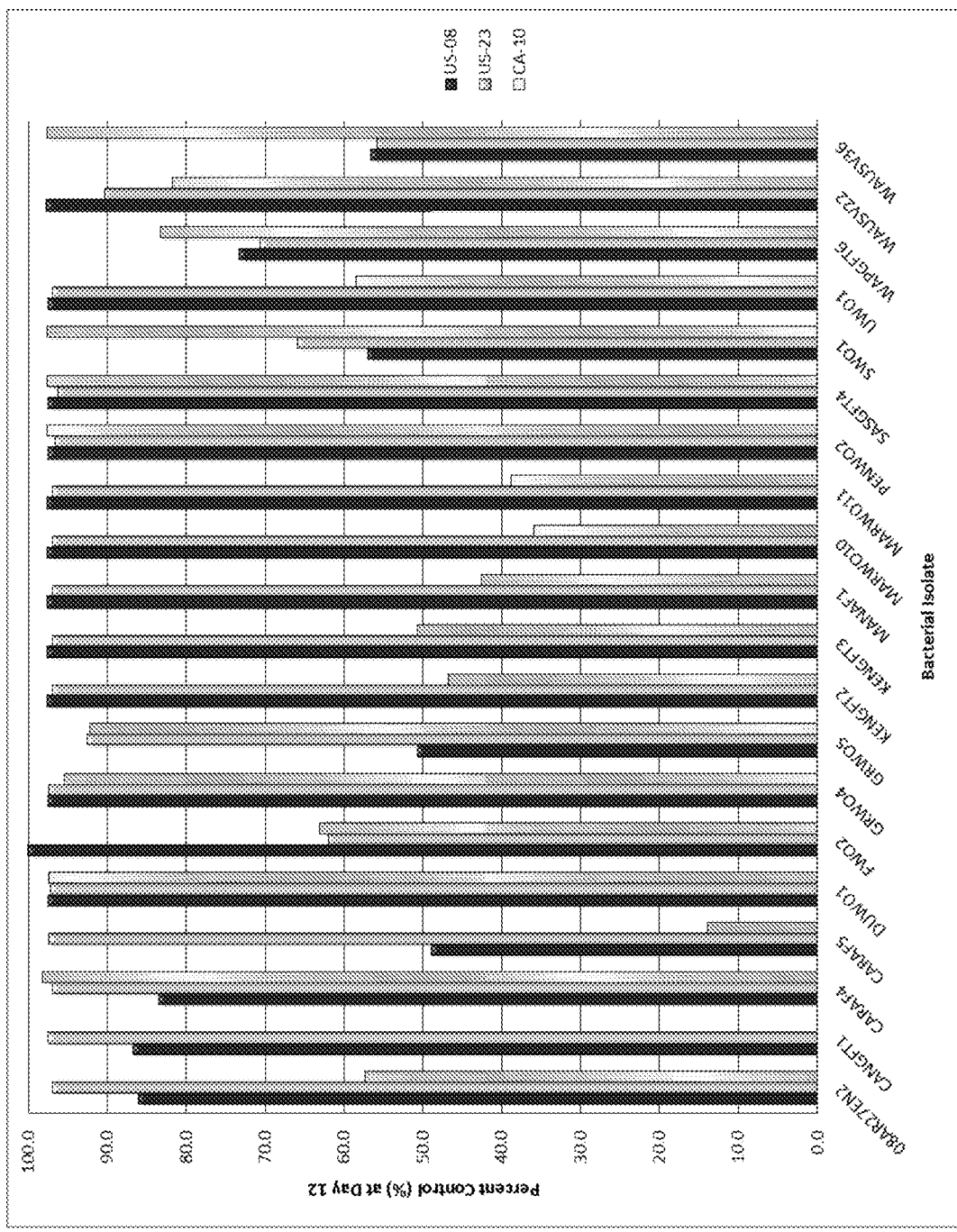
FIG. 1 is a bar graph showing the percent control of growth of *Phytophthora infestans* genotypes US-08, US-23 and CA-10 by various bacterial strains in vitro.

The present invention provides one or more strains of bacteria, or a culture thereof, which are useful as biopesticides against the pathogen *Phytophthora infestans*, the causative agent for potato late blight disease. Bacterial strains were obtained for initial screening from a culture collection established by Dr. Susan Boyetchko (Agriculture and Agri-Food Canada). Bacteria in the collection were isolated and purified from rhizosphere soils, roots or seeds collected from across the Canadian prairies. In at least one embodiment, the bacterial strain is selected from *Pseudomonas chlororaphis* strain 189, *Bacillus subtilis* strain WAUSV36, *Pseudomonas fluorescens* strain UWO1, *Pseudomonas fluorescens* strain KENGFT3, *Arthrobacter* sp. strain OY3WO11 and *Pantoea* sp. strain OXWO6B1.

A deposit of *Pseudomonas chlororaphis* strain 189 pursuant to the Budapest Treaty was received on Nov. 17, 2016 by the International Depositary Authority of Canada (IDAC), National Microbiology Laboratory, Public Health Agency of Canada, 1015 Arlington Street, Winnipeg, Manitoba, Canada R3E 3R2 (Accession number: 151116-02). The full genome of *Pseudomonas chlororaphis* strain 189 has been deposited at DDBJ (DNA Databank of Japan)/EMBL (European Molecular Biology Laboratory European Nucleotide Archive (ENA))/GenBank under accession number CP014867 (Town et al., *Genome Announcements* (May/June 2016) 4(3): e00581-16).

A deposit of *Bacillus subtilis* strain WAUSV36 was received by IDAC on Nov. 17, 2016 (Accession number: 151116-01). A draft genome sequence of *Bacillus subtilis* strain WAUSV36 has been deposited at DDBJ/EMBL/GenBank under accession numbers LWLQ00000000 and LWLQ01000000 (Town et al., *Genome Announcements* (May/June 2016) 4(3): e00586-16).

A deposit of *Pseudomonas fluorescens* strain UWO1 was received by IDAC on Nov. 17, 2016 (Accession number: 151116-03).

A deposit of *Pseudomonas fluorescens* strain KENGFT3 was received by IDAC on Nov. 17, 2016 (Accession number: 151116-05). A draft genome sequence of *Pseudomonas fluorescens* strain KENGFT3 has been deposited at DDBJ/EMBL/GenBank under accession number CP014868 (Town et al., *Genome Announcements* (May/June 2016) 4(3): e00428-16).

A deposit of *Arthrobacter* sp. strain OY3WO11 was received by IDAC on Nov. 17, 2016 (Accession number: 151116-04). A draft genome sequence of *Arthrobacter* sp. strain OY3WO11 has been deposited at DDBJ/EMBL/GenBank under accession numbers LWLP00000000 and LWLP01000000 (Town et al., *Genome Announcements* (May/June 2016) 4(3): e00585-16).

A deposit of *Pantoea* sp. strain OXWO6B1 was received by IDAC on Nov. 17, 2016 (Accession number: 151116-06). A draft genome sequence of *Pantoea* sp. strain OXWO6B1 has been deposited at DDBJ/EMBL/GenBank under accession numbers LWLR00000000 and LWLR01000000 (Town et al., *Genome Announcements* (May/June 2016) 4(3): e00582-16).

In at least one embodiment, the bacterial strain is effective to control, treat or prevent potato late blight disease in one or more solanaceous crops. In at least one embodiment, the bacterial strain is effective to control, treat or prevent infection of one or more solanaceous crops by *Phytophthora infestans*. In at least one embodiment, the solanaceous crop is potato. In at least one embodiment, the solanaceous crop is tomato.

The present invention also provides an extract from one or more biopesticidal bacterial strains as described herein. In at least one embodiment, the extract is an extract of a culture medium in which the one or more biopesticidal bacterial strains have grown. In at least one embodiment, the extract is a cell-free extract. In at least one embodiment, the cell-free extract contains one or more compounds having antifungal activity against *Phytophthora infestans*. In at least one embodiment, the one or more compounds having antifungal activity against *Phytophthora infestans* are bacterial secondary metabolites. In at least one embodiment, the extract of the bacterial strain is effective to control, treat or prevent potato late blight disease in one or more solanaceous crops, or to control, treat or prevent infection of one or more solanaceous crops by *Phytophthora infestans*.

Without being limited by theory, it is contemplated that the bacterial culture, or extract thereof, can exert antifungal activity against *Phytophthora infestans* by one or more mechanisms. In at least one embodiment, the bacteria can act to induce or prevent the expression of one or more genes in *Phytophthora infestans*, thereby causing an antifungal effect. In at least one embodiment, the bacteria can produce one or more compounds, including but not limited to secondary metabolites, which can exert antifungal activity against *Phytophthora infestans*. In at least one embodiment, the bacteria can act to induce resistance in the host plant to infection by *Phytophthora infestans*. In at least one embodiment, the bacteria can act to induce the expression of one or more genes in the host plant which cause the host plant to be more resistant to infection by *Phytophthora infestans* than the host plant would be in the absence of the bacteria. In at least one embodiment, the bacteria can act to prevent the expression of one or more genes in the host plant which cause the host plant to be more susceptible to infection by *Phytophthora infestans* than the host plant would be in the presence of the bacteria.

In at least one embodiment, the bacterial strain, or an extract thereof, including but not limited to a cell-free extract thereof, can be formulated into a biopesticidal formulation for application to solanaceous crops in danger of infection by *Phytophthora infestans* or of potato late blight disease. In at least one embodiment, the biopesticidal formulation comprises the bacterial strain or extract thereof and one or more agriculturally acceptable carriers. Other additives known in the art which can beneficially modify the properties of the formulation can also be present. Such additives can, for example, modify or improve one or more of the convenience or ease of handling or application, efficacy, safety or cost effectiveness of the formulation. The skilled person would be aware of ways in which to prepare such formulations and to test the prepared formulations for efficacy, in light of the further teachings herein.

Also contemplated is a method of controlling, treating or preventing potato late blight disease in plants. The method includes applying a bacterial culture as described herein, or an extract thereof, or a biopesticidal formulation thereof, to a plant, or part thereof, infected by, or at risk of infection by, *Phytophthora infestans*. The bacterial culture, extract thereof, or biopesticidal formulation thereof can be in any form useful for such application, as known in the art, and can be applied by any known method, and at any stage in the plant lifecycle at which application of the bacterial culture, extract thereof, or biopesticidal formulation thereof will be effective at controlling, treating or preventing potato late blight disease or infection by *Phytophthora infestans*.

In at least one embodiment, the bacterial culture, extract thereof, or biopesticidal formulation thereof is applied by spraying. In at least one embodiment, the bacterial culture, extract thereof, or biopesticidal formulation thereof is applied to plants growing in the field. In at least one embodiment, the bacterial culture, extract thereof, or biopesticidal formulation thereof is applied to plants under cultivation, including but limited to cultivation in greenhouses or glasshouses. In at least one embodiment, the bacterial culture, extract thereof, or biopesticidal formulation thereof is applied to tubers prior to or during storage. In at least one embodiment, the tubers are potato tubers. In at least one embodiment, the bacterial culture, extract thereof, or biopesticidal formulation thereof is applied to fruit before harvest. In at least one embodiment, the bacterial culture, extract thereof, or biopesticidal formulation thereof is applied to fruit after harvest. In at least one embodiment the fruit is tomato fruit.

EXAMPLES

Other features of the present invention will become apparent from the following non-limiting examples which illustrate, by way of example, the principles of the invention.

Example 1

Culture of Microorganisms

Bacterial Suspensions:

Bacterial cultures maintained at −80° C. are thawed and grown on *Pseudomonas Agar* F media (Difco™ pancreatic digest of casein (10.0 g), proteose peptone No. 3 (10.0 g), $K_2HPO_4$ (1.5 g), $MgSO_4$ (1.5 g), agar (15.0 g) and glycerol (10 g) in water (1 L)). Colonies are inoculated into 125 mL of yeast extract glucose medium (YGM; yeast extract (2.0 g), dextrose (2.5 g), buffer solution (10 mL, $KH_2PO_4$ (25.0 g/L) and $K_2HPO_4$ (25.0 g/L)), and saline solution (10 mL, $MgSO_4.7H_2O$ (10.0 g/L), $MnSO_4.H_2O$ (1.5 g/L), NaCl (5.0 g/L) and $FeSO_4.7H_2O$ (0.5 g/L)) in water (1 L total volume)) and incubated for 48 h on a rotary shaker (150 rpm) in 500 mL baffled flasks at 22° C. to provide bacterial suspensions.

Cell-Free Bacterial Filtrates:

Bacterial suspensions are centrifuged at 10,000 rpm for 10 minutes and the supernatant is vacuum filtered through a 0.22 μm non-protein binding filter to provide cell-free bacterial filtrates.

*Phytophthora infestans* Cultures

*Phytophthora infestans* isolates genotypes CA-10 (A1 mating type from tomato), US-08 (A2 mating type from potato) and US-23 (A1 mating type from potato) are used for in vitro testing. *Phytophthora infestans* isolates genotypes CA-09 (A1 mating type from tomato), CA-10 (A1 mating type from tomato), US-08 (A2 mating type from potato and US-22 (A2 mating type from tomato) are used for in vivo testing. All *Phytophthora infestans* isolates are maintained on Rye Seed A agar (RSA) (Caten, C. E. and J. L. Jinks. "Spontaneous variability of single isolates of *Phytophthora infestans*. I. Cultural variation." *Can. J. Bot.* (1968) 46: 329-348).

Example 2

In Vitro Bioassays

Bacterial Suspensions

An agar plug (0.5 cm diameter) of *Phytophthora infestans* (A1 or A2 mating types) is placed in the centre of a Petri dish (9 cm diameter) containing Rye Seed A agar (RSA). An aliquot (2 μL) of bacterial suspension is placed near the edge of the plate; 2-4 bacterial strains are tested on each plate. Zones of inhibition are measured after incubation at 15° C. for 7 days. Experiments are conducted twice, using four replicates each.

Cell-Free Bacterial Filtrates

Cell-free bacterial filtrates, or sterile water as a negative control, are dispensed in agar (50%, v/v). A mycelial plug of the pathogen is placed in the centre of a Petri dish (9 cm diameter) and mycelial growth is measured after incubation at 22° C. for 7 and 12 days. Experiments are conducted twice, using four replicates each. Results are analyzed using SAS™ software. Percent control (%) is calculated as follows:

Percent Control (%)=100−(B/C×100)

where B is the mean growth observed in the presence of bacterial filtrate at Day 7 or Day 12 and C is the mean growth observed in the presence of sterile water (control) at Day 7 or Day 12.

Results

Bacterial strains from a culture collection established by Dr. Susan Boyetchko (Agriculture and Agri-Food Canada) originating from a variety of soils and plant roots collected from the Canadian prairies and representing diverse taxonomic groups were tested as bacterial suspensions in the in vitro assay described above. Forty-six strains showed activity in this assay and were selected for further testing. FIG. 1 shows the percent control at Day 12 for cell-free filtrates of 20 of these selected bacterial strains against genotypes CA-10 (A1, tomato), US-08 (A2, potato) and US-23 (A1, potato) of *Phytophthora infestans*. As seen from FIG. 1, most of the cell-free extracts of the bacterial strains tested show significant inhibitory activity against one or more genotypes of *Phytophthora infestans*.

Example 3

In Vivo Fed Detached Leaf Bioassay

Potato leaves containing 5 leaflets each are selected and grown in 50 mL test tubes containing 10% Hoagland's solution (Hoagland, D. R., and Arnon, D. I. "The water-culture method for growing plants without soil" Univ. Calif. Coll. Agric. Exp. Sta. Circ. Berkeley, Calif. (1938), 347-353). The leaves are dipped in the selected test or control treatment as described below, followed 2 h later by spraying until runoff with a suspension of *Phytophthora infestans*. Treated leaves are incubated at 22° C. under high humidity conditions (86-92% relative humidity) and a photoperiod of 16 h day/8 h night.

Disease progression and severity on leaves are measured after 7 and 10 days incubation by estimating the proportion of photosynthetic area affected by the pathogen (James, 1971: James, W. C. An Illustrated Series of Assessment Keys for Plant Diseases, their Preparation and Usage. *Canadian Plant Disease Survey* (1971) 51(2), 39-65). The area of disease coverage is scored individually (out of a maximum of 20) for each of the five leaflets, and the scores for the individual leaflets are added to give a total score (out of a maximum of 100) for each leaf. The percent disease severity is determined by dividing the disease severity rating of treated leaves by the disease severity rating of leaves exposed to pathogen alone, and multiplying the result by 100%.

Results

The forty-six selected bacterial strains were tested in the in vivo fed detached leaf bioassay described above, using 12 leaves per treatment. Experiments were replicated twice. Each set of 12 leaves was treated by dipping in one of a bacterial suspension prepared as in Example 1, a cell-free bacterial filtrate prepared as in Example 1, an autoclaved (20 minutes, 121 psi) bacterial suspension, or YGM medium alone (control), prior to exposure to *Phytophthora infestans* (10,000 sporangia/mL; US-08 isolate).

Figure 2:
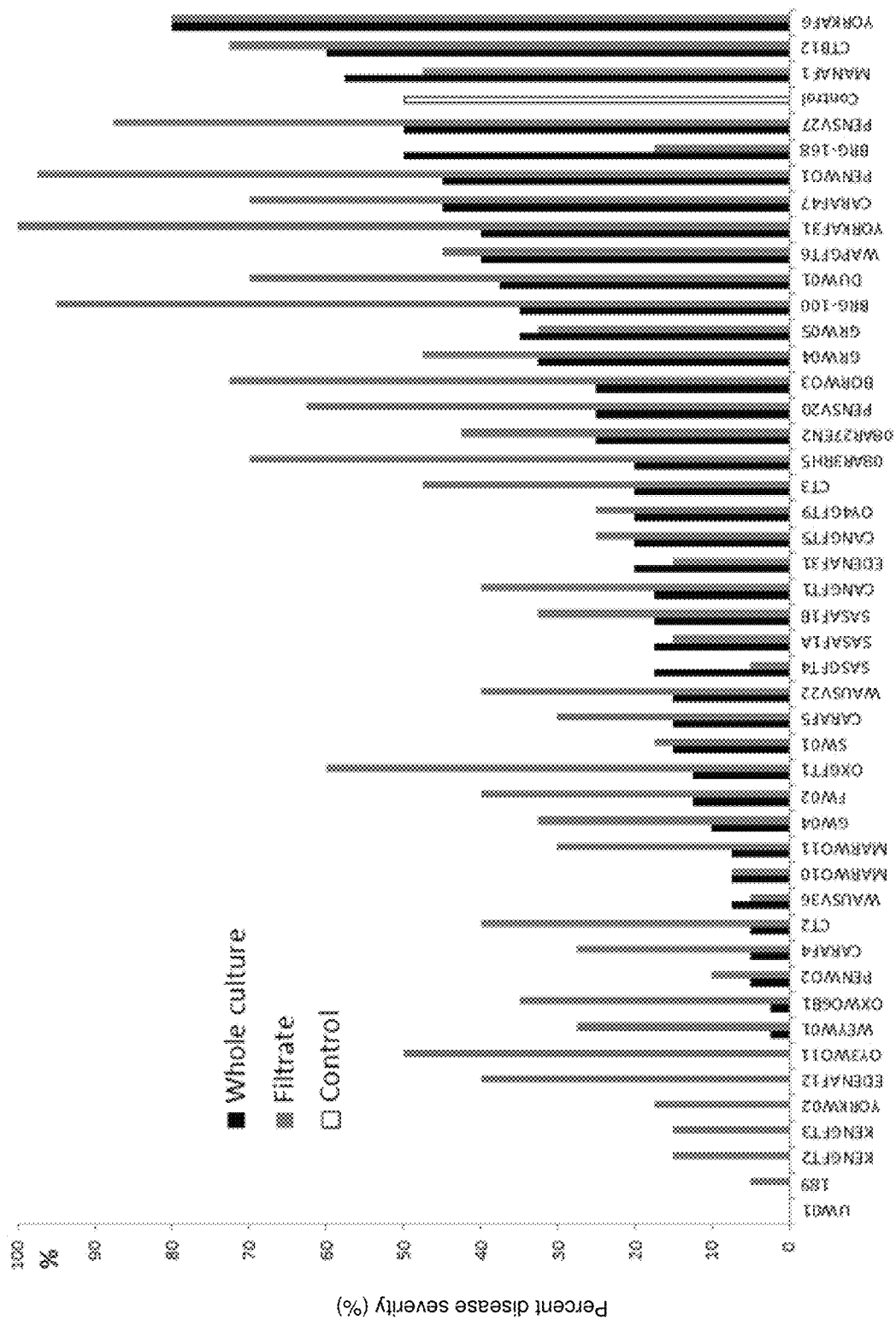
FIG. 2 is a bar graph showing the percent disease severity in potato leaves infected with *Phytophthora infestans* genotype US-08 in the presence of various bacterial suspensions and cell-free bacterial filtrates.
Figure 3:
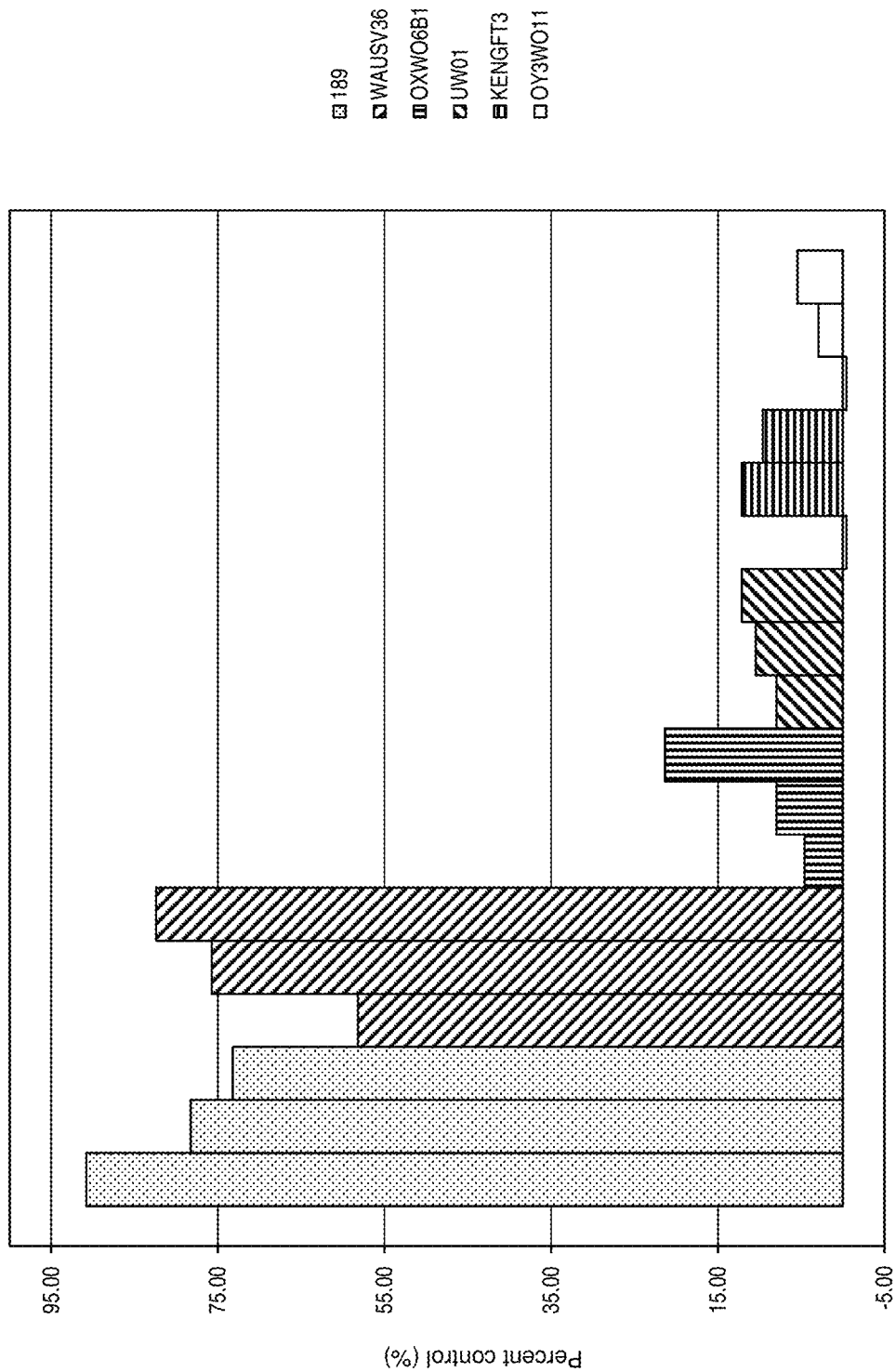
FIG. 3 is a bar graph showing the percent control of growth of *Phytophthora infestans* genotype CA-09 (A1) in potato leaves 10 days after infection in the presence of various bacterial suspensions.
Figure 4:
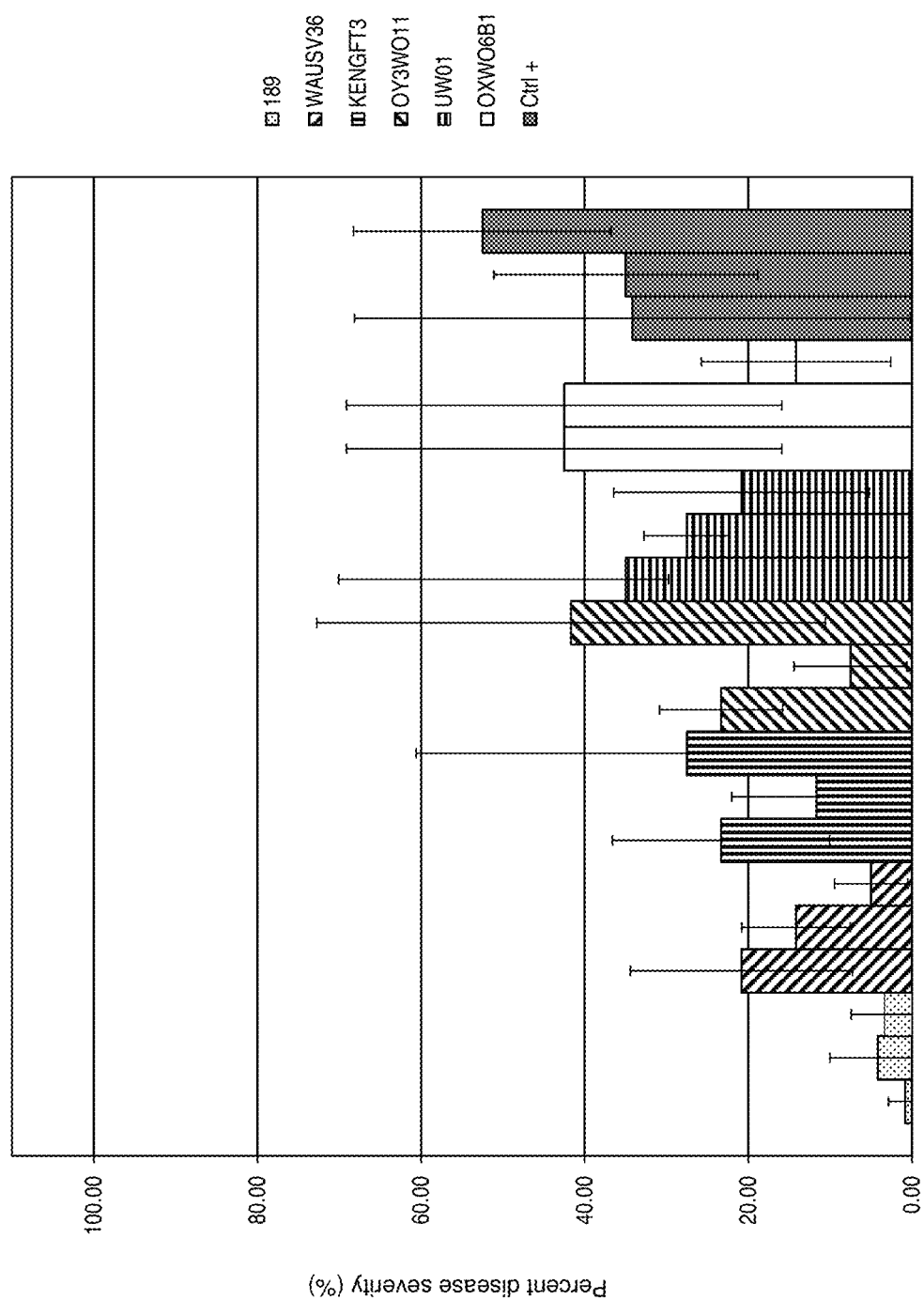
FIG. 4 is a bar graph showing the percent disease severity in potato leaves infected with *Phytophthora infestans* genotype US-22 (A2) 7 days after infection in the presence of various bacterial suspensions.
Figure 5:
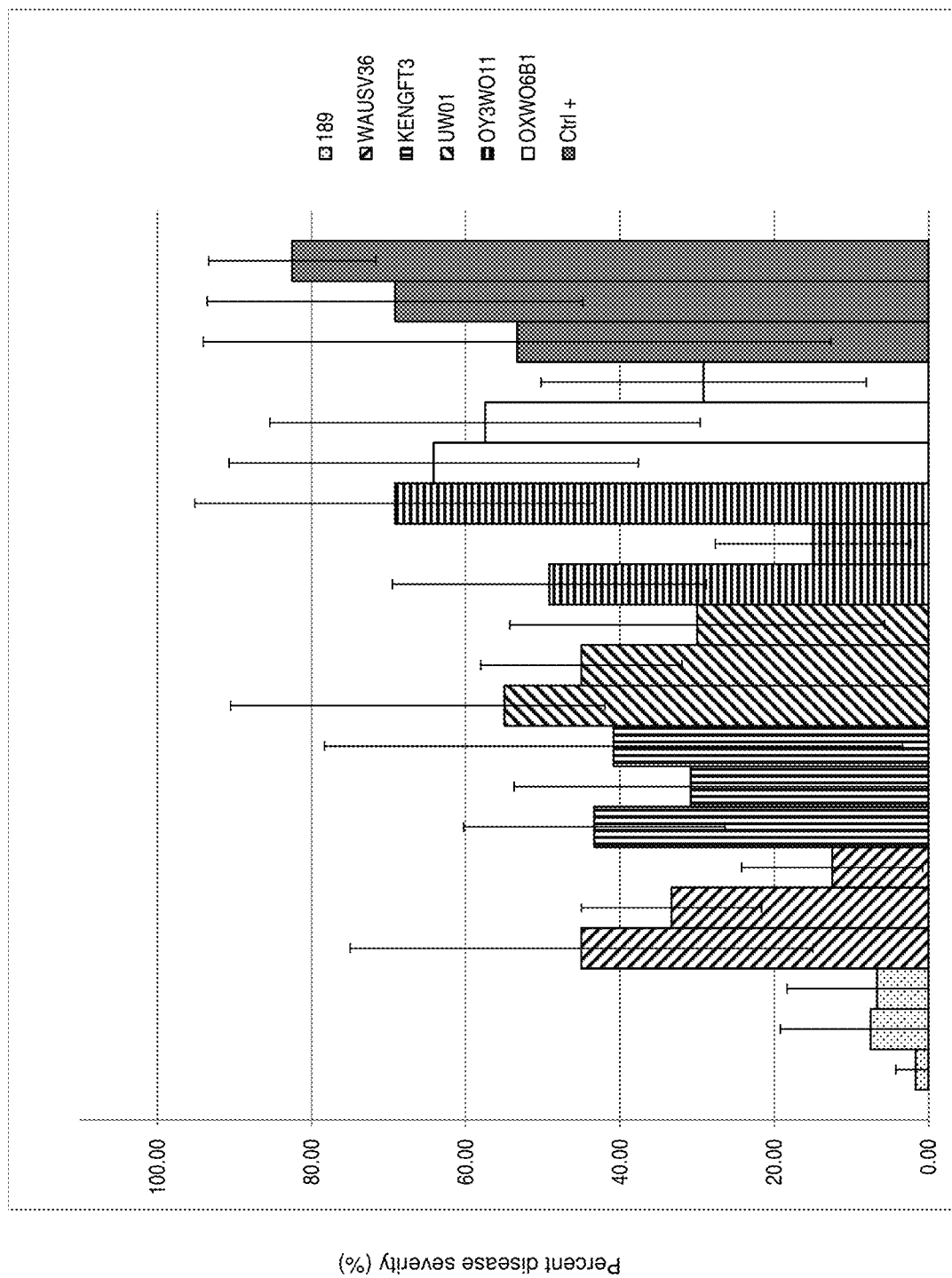
FIG. 5 is a bar graph showing the percent disease severity in potato leaves infected with *Phytophthora infestans* genotype US-22 (A2) 10 days after infection in the presence of various bacterial suspensions.

FIG. 2 shows the percent disease severity of infected leaves treated with bacterial suspensions and cell-free bacterial filtrate from 46 test bacterial strains 10 days after treatment and inoculation with *Phytophthora infestans*. The bacterial strains are arranged in order of increasing disease severity of leaves exposed to whole culture (bacterial suspension), from left to right. Thus, bacterial strains for which the whole culture is most effective against *Phytophthora infestans* are identified at the left of the chart.

Six bacterial strains were selected for further investigation, based on the effects of whole bacterial cultures to control disease severity caused by *Phytophthora infestans*. The six bacterial strains were tested in the in vivo fed detached leaf bioassay described above, using 18 leaves per treatment. Experiments were replicated four times. Each set of 18 leaves was treated by dipping in a 48-hour bacterial suspension prepared as in Example 1, or distilled water, prior to exposure to *Phytophthora infestans* (7,000 sporangia/mL). Each of the CA-09 (A1), CA-10 (A1), US-08 (A2) and US-22 (A2) genotypes of *Phytophthora infestans* was tested in a separate experiment. The percent disease severity of leaves exposed to *Phytophthora infestans* (US-08 (A2) isolate) in the presence of the six selected bacterial strains is shown in Table 1.

TABLE 1

| | Bacterial strains | | | | | |
|---|---|---|---|---|---|---|
| Treatment | UW01 | KENGFT3 | OY3WO11 | 189 | OXWO6B1 | WAUSV36 |
| Bacterial suspension + Pathogen | 0 | 2 | 2 | 1 | 5 | 7 |
| Cell-free bacterial filtrate + Pathogen | 1 | 15 | 52 | 7 | 36 | 8 |
| Autoclaved culture + Pathogen | 39 | 75 | 39 | 23 | 37 | 0 |
| Pathogen Alone | 23 | 82 | 58 | 23 | 58 | 33 |

As seen from the data in Table 1, all six bacterial strains protect potato leaves from the effects of infection by *Phytophthora infestans* genotype US-08 (A2) when applied as a bacterial suspension. In addition, cell-free isolates of strains UWO1, KENGFT3, 189 and WAUSV3 show significant protection of potato leaves from the effects of infection by *Phytophthora infestans* genotype US-08 (A2).

As can be seen from FIG. 3, strains 189 and WAUSV36 show the best percent control of growth of *Phytophthora infestans* genotype CA-09 (A1). As well, FIGS. 4 and 5 show that strain 189 protects potato leaves against infection with *Phytophthora infestans* genotype US-22 (A2) better than the five other strains tested. Table 2 shows a comparison of the efficacy of treatment with bacterial suspensions of each of the six tested bacterial strains against four genotypes of *Phytophthora infestans* compared to treatment with distilled water (control). SS indicates that the results from treatment with the bacteria are statistically significantly better than those from treatment with control at the p=0.01 level; NSS indicates that the difference between treatment with bacteria and control is not statistically significant at the p=0.01 level.

TABLE 2

| Bacterial | *Phytophthora infestans* genotype | | | |
|---|---|---|---|---|
| strains | US-08 (A2) | CA-10 (A1) | CA-09 (A1) | US-22 (A2) |
| 189 | SS | SS | SS | SS |
| WAUSV36 | SS | SS | SS | NSS |
| KENGFT3 | SS | SS | NSS | NSS |
| UW01 | SS | SS | NSS | NSS |
| OXWO6B1 | SS | NSS | NSS | NSS |
| OY3WO11 | SS | NSS | NSS | NSS |

Example 4

Identification of Bacteria

Bacterial suspensions (200 μL, prepared as in Example 1) are boiled for 5 min, then cooled to room temperature and centrifuged. The supernatant (2 μL) is subjected to PCR (polymerase chain reaction) conditions to amplify the internal transcribed spacer (ITS) and chaperonin 60 universal target (cpn60 UT) regions of the bacterial genome. ITS regions are amplified and bands are sized to group similar strains, so as to avoid repetitive sequencing of highly similar or identical cpn60 UT sequences from closely related strains.

ITS amplicons are generated with primers ITS-F and ITS-R as described in Schellenberg et al., "Selection, phenotyping and Identification of acid and hydrogen peroxide producing bacteria from vaginal samples of Canadian and East African women." PLoS One (2012) 7(7): e41217. Bands are sized by electrophoresis on a polyacrylamide gel (4-20% gradient gels, Invitrogen) and post-stained using SYBR™ Green I stain (Invitrogen). Gels are imaged with a Bio-Rad gel imager and bands are sized by comparison to molecular weight markers.

The cpn60 UT sequences of bacterial isolates are determined by directly sequencing amplicons generated using M13-adapted universal primers H729/H730 as described in Goh et al., "Identification of *Enterococcus* species and phenotypically similar *Lactococcus* and *Vagococcus* species by reverse checkerboard hybridization to chaperonin 60 gene sequences." Journal of Clinical Microbiology (2000) 38: 3953-3959. Samples with higher G/C content (e.g. *Pseudomonas* spp.) were amplified successfully using M13-adapted cpn60 UT "magic" primers H1594: (5'-CGCCAGGGTTTTCCCAGT-CACGACGACGTCGCCGGTGACGGCACCACCAC-3' (SEQ ID NO:1) and H1595:
5'-AGCGGATAACAATTTCACACAGGACGA CGGTCGCCGAAGCCCGGGGCCTT-3' (SEQ ID NO:2) (primers courtesy of Dr. Sean Hemmingsen, National Research Council of Canada). PCR conditions include 1U Taq DNA polymerase (Invitrogen), 2.5 mM $MgCl_2$, 500 nM of each dNTP, and 400 nM of each of forward and reverse primer sets, for one cycle at 95° C. for 3 min and 40 cycles at 95° C. for 30 sec, 50° C. for 30 sec, and 72° C. for 30 sec.

In some cases, amplicons are generated with a 3:1 molar ratio of primers H1612-H1613 and H279-H280, as described in Hill et al., "Improved template representation in cpn60 polymerase chain reaction (PCR) product libraries generated from complex templates by application of a specific mixture of PCR primers." Environmental Microbiology (2005) 8: 741-746, and are cloned into a pGEM™-T Easy vector (Promega) prior to sequencing. Amplicons are purified using QiaQuick™ PCR purification kit (Qiagen) or using Amicon™ YM-30 ultrafiltration membranes (Fisher), and sequenced. Plasmids are prepared with a QuickLyse™ plasmid kit (Qiagen) prior to sequencing.

Results

Some bacterial strains which were found to be effective at controlling *Phytophthora infestans* infection were identified by comparing the sequences of the chaperonin 60 universal target (cpn60 UT) regions of the bacterial genome to corresponding sequences from known bacterial strains. Initial identification is carried out by comparison to reference databases, including but not limited to the chaperonin database (Hill J. E. et al., "cpnDB: a chaperonin sequence database" *Genome Res*. (2004) 14:1669-1675) and the National Center for Biotechnology Information (NCBI) database, complemented by the construction of phylogenetic trees. Based on this comparison, the six bacterial strains selected for further investigation were identified as follows:

189 *Pseudomonas chlororaphis* strain 189
KENGFT3 *Pseudomonas fluorescens* strain KENGFT3
OXWO6B1 *Pantoea* sp. strain OXWO6B1
OY3WO11 *Arthrobacter* sp. strain OY3WO11
UWO1 *Pseudomonas fluorescens* strain UWO1
WAUSV36 *Bacillus subtilis* strain WAUSV36

Example 5

Sequencing of Bacterial Genomes

*Pseudomonas chlororaphis* Strain 189

Genomic DNA was purified from 1 mL of an overnight culture in YGM (Example 1) of *Pseudomonas chlororaphis* strain 189 using a Wizard genomic DNA (gDNA) extraction kit (Promega, Madison, Wis., USA) and sequenced on the MiSeq platform using the mate-pair protocol (Illumina), generating 2.8 Mb of mate-pair reads. An additional 8-kb insert paired-end sequencing run was performed based on the paired-end rapid library preparation protocol for Titanium chemistry (Roche, March 2012), with modifications as described (Hill et al., Protocol Exchange (2014) doi: 10.1038/protex.2014.028), generating 166,514 paired-end reads with an estimated pair distance of 5,641±1,410 bp.

Illumina reads were assembled using SOAPdenovo2 version 2.01 (Luo et al.: SOAPdenovo2: an empirically improved memory-efficient short-read de novo assembler. GigaScience (2012) 1: 18.) with k-mer size 127 and map length 34. The resulting 957 contigs ($N_{50}$ 33,267 bp) were split into 500-bp pieces with a 200-bp overlap using EMBOSS splitter, combined with the Roche paired-end reads, and reassembled using Newbler version 3.0 (454 Life Sciences). Gaps in the sequence were filled using the GapCloser tool for SOAPdenovo2, along with PCR and Sanger sequencing. Assembly of all sequencing data together produced a finished 6.8-Mbp genome sequence (SEQ ID NO:3) with 152× coverage, featuring a single scaffold with no gaps and no evidence of any plasmids. Sequence data were annotated using the Prokaryotic Genome Annotation Pipeline version 3.1 (NCBI).

The genome of *Pseudomonas chlororaphis* strain 189 contains 6,837,781 bp (62.74% G/C); 6,025 genes and 5,934 protein-encoding genes were observed, along with 6 genes encoding 5S rRNA, 5 genes encoding 16S rRNA, 5 genes encoding 23S rRNA, and 71 tRNA-encoding genes. Moreover, 2,075 clusters of orthologous groups were identified by annotation using the Integrated Microbial Genomes portal.

Examination of the cpn60 sequence of*Pseudomonas chlororaphis* strain 189 suggests that this strain is most closely related to *Pseudomonas chlororaphis* subsp. *aureofaciens* 30-84 (NZ_CM001559.1), with a nucleotide identity of 99.6%. Consistent with this observation, determination of the genome-level average nucleotide identity with 14 other genomes from this species revealed that *Pseudomonas chlororaphis* strain 189 shares the highest genome sequence identity (98.36%) with this strain. Several other strains of *Pseudomonas chlororaphis* exhibiting biocontrol phenotypes, including PA23, have genome similarity metrics that place them in the same species as*Pseudomonas chlororaphis* strain 189. Like PA23, *Pseudomonas chlororaphis* strain 189 contains an array of biosynthetic pathways capable of producing metabolites involved in biocontrol, including hydrogen cyanide, phenazine, pyocin, pyrroloquinoline quinone, and cell wall degradative enzymes. Genes conferring the ability to produce surfactants and form biofilms were also found. The sequence data for this complete genome has been deposited at DDBJ/EMBL/GenBank under accession number CP014867 (Town et al., *Genome Announcements* (May/June 2016) 4(3): e00581-16).

*Pseudomonas fluorescens* Strain KENGFT3

Genomic DNA was purified from 1 mL of an overnight culture in YGM (Example 1) of *Pseudomonas fluorescens* strain KENGFT3 using a Wizard genomic DNA (gDNA) extraction kit (Promega, Madison, Wis., USA) and sequenced on the GS Junior using Titanium Plus chemistry (Roche Diagnostics, Laval, Quebec, Canada). Reads from two shotgun sequencing runs with average read lengths of 548 and 534 bp were assembled using Newbler version 3.0 (454 Life Sciences). The total number of filter-passed reads was 128,460, and the total number of bases assembled was 69,421,957. These reads were assembled into 97 large contigs, with an $N_{50}$ contig size of 131,172 kbp.

In addition, an 8-kb-insert paired-end sequencing run was performed based on the paired-end rapid library preparation protocol for Titanium chemistry (Roche), with modifications as described (Hill et al., Protocol Exchange (2014) doi: 10.1038/protex.2014.028). A total of 105,459 paired-end reads were generated, with an estimated pair distance of 6,361±1,590 bp. Assembly of all the sequencing runs together produced an improved high-quality draft sequence featuring 16× genome coverage of a single scaffold with 9 scaffold contigs (SEQ ID NO:4 to SEQ ID NO:12, Table 3). Sequence data were annotated using the Prokaryotic Genome Annotation Pipeline version 2.0 (NCBI).

TABLE 3

| Contig | Location in genome | Number of base pairs | Sequence |
|---|---|---|---|
| 1 | 1 to 1127585 | 1127585 | SEQ ID NO: 4 |
| 2 | 1132047 to 1134857 | 2811 | SEQ ID NO: 5 |
| 3 | 1135358 to 1187082 | 51725 | SEQ ID NO: 6 |
| 4 | 1187731 to 1902001 | 714271 | SEQ ID NO: 7 |
| 5 | 1902220 to 2952001 | 1048002 | SEQ ID NO: 8 |
| 6 | 2950759 to 4502624 | 1551866 | SEQ ID NO: 9 |
| 7 | 4502688 to 4522603 | 19916 | SEQ ID NO: 10 |
| 8 | 4522629 to 5334906 | 812278 | SEQ ID NO: 11 |
| 9 | 5335136 to 6183292 | 848157 | SEQ ID NO: 12 |

The genome of *Pseudomonas fluorescens* strain KENGFT3 contains 6,183,292 bp (59.95% G+C content). A total of 5,791 genes and 5,549 protein-coding genes were observed, along with 6 genes encoding 5S rRNA, 5 genes encoding 16S rRNA, 5 genes encoding 23S rRNA, and 64 tRNA-coding genes. The majority (77.76%) of protein-coding genes had a predicted function, and 2,053 COG clusters were identified.

The species identification tool SpecI (Mende et al., Nat Methods (2013), 10: 881-884) could not assign *Pseudomonas* sp. strain KENGFT3 to a species cluster (the average nucleotide identity was 95.1% to *Pseudomonas fluorescens* strain SBW25; GenBank accession no. NC_012660.1). JSpecies (Richter et al., Proc Natl Acad Sci USA (2009) 106: 19126-19131) also revealed that *Pseudomonas* sp. strain KENGFT3 had genome comparison metrics that placed it below the identified cutoff for inclusion in the same species as *Pseudomonas fluorescens* SBW25. However, *Pseudomonas fluorescens* strain LBUM223, which shares certain phenotypic attributes with strain KENGFT3, had genome comparison metrics that place these two strains within the same species (average nucleotide identity (ANI), 99.39%). Calculation of a phylogenetic distance tree using 60 strains of *Pseudomonas fluorescens* annotated at the Integrated Microbial Genomes portal revealed that *Pseudomonas fluorescens* strains KENGFT3 and LBUM223 clustered with *Pseudomonas fluorescens* strains GcM5-1A and UK4. *Pseudomonas fluorescens* strain KENGFT3 possesses an array of genes that have been associated with biocontrol phenotypes, including phenazine carboxylic acid synthesis, chitinases and cellulases, and pyrroloquinoline quinone biosynthesis, among others. Ten genes encoding putative β-lactamases were also found. The sequence data for this complete genome have been deposited at DDBJ/EMBL/GenBank under the accession no. CP014868 (Town et al., *Genome Announcements* (May/June 2016) 4(3): e00428-16).

*Pantoea* sp. strain OXWO6B1

Genomic DNA was purified from 1 mL of an overnight culture in YGM (Example 1) of *Pantoea* sp. strain OXWO6B1 using a Wizard genomic DNA (gDNA) extraction kit (Promega, Madison, Wis., USA). Genomic shotgun sequencing was performed on the MiSeq platform (Illumina), generating 2.9 M paired-end reads. These data were supplemented by an 8-kb-insert paired-end sequencing run using the paired-end rapid library preparation protocol for Titanium chemistry (Roche, March 2012), with modifications as described previously (Hill et al., Protocol Exchange (2014) doi:10.1038/protex.2014.028). This process generated 187,389 paired-end reads with an estimated pair distance of 6,310±1,577 bp.

Illumina reads were assembled using SOAPdenovo2 (version 2.01), with kmer size of 127 and map length of 34. The resulting 690 contigs ($N_{50}$, 44,093 bp) were split into 500-bp pieces with a 200-bp overlap using the EMBOSS splitter, combined with the Roche paired-end reads, and reassembled using Newbler (version 3.0). Gaps in the sequence were filled using the GapCloser tool for SOAPdenovo2, along with PCR and Sanger sequencing. Assembly of all the sequencing data together produced a high-quality draft genome sequence with 201× coverage featuring 2 scaffolds of 4,677,766 bp (2 scaffold contigs; the first containing residues 1 to 200112 (SEQ ID NO:13) and the second containing residues 200566 to 4677766 (SEQ ID NO:14)) and 118,792 bp (single contig; SEQ ID NO:15), respectively. Three plasmids of 253,747 bp (SEQ ID NO:16), 181,185 bp (SEQ ID NO:17), and 4650 bp (SEQ ID NO:18) were confirmed using PCR. Sequence data were annotated using the Prokaryotic Genome Annotation Pipeline version 3.1 (NCBI) and the Integrated Microbial Genomes portal.

The genome of *Pantoea* sp. strain OXWO6B1 is 5,236,140 bp (52.74% G+C content). A total of 5,030 genes and 4,868 protein-coding genes were identified, along with 10 genes encoding 5S rRNA, 7 genes encoding 16S rRNA, 7 genes encoding 23S rRNA, and 78 tRNA-coding genes.

The sequences of the taxonomic markers 16S rRNA and rpoB suggest that strain OXWO6B1 is most closely related to *Pantoea ananatis*, with 99% (16S) and >97% (rpoB) identity to *Pantoea ananatis*. However, the bacterial barcode marker cpn60 has a lower sequence identity with any *Pantoea* sp. (the nearest neighbor was *Pantoea stewartii*, with 93.7% sequence identity). Consistent with this, the genomic average nucleotide identity (ANI) of strain OXWO6B1 was below the specified cutoff for species identity with any reported species of *Pantoea*, with a maximum of 88.9% ANI with *Pantoea ananatis*. Moreover, a comparison of 40 Clusters of Orthologous Groups (COGs) using SpecI (Mende et al., Nat Methods (2013), 10: 881-884) revealed that *Pantoea* sp. strain OXWO6B1 could not be assigned to a species cluster (average nucleotide identity was 95.0% to *Pantoea ananatis*). *Pantoea* sp. strain OXWO6B1 contains genes that have been associated with biocontrol phenotypes, including phenazine carboxylic acid synthesis and cell wall-degradative enzymes. Two genes encoding putative beta-lactamases were also observed. This whole-genome shotgun project has been deposited at DDBJ/ENA/GenBank under the accession nos. LWLR00000000 and LWLR01000000 (Town et al., *Genome Announcements* (May/June 2016) 4(3): e00582-16).

*Arthrobacter* sp. strain OY3WO11

Genomic DNA was purified from 1 mL of an overnight culture in YGM (Example 1) of *Arthrobacter* sp. strain OY3WO11 using a Wizard genomic DNA (gDNA) extraction kit (Promega, Madison, Wis., USA) and sequenced on the GS Junior using Titanium Plus chemistry (Roche Diagnostics, Laval, Quebec, Canada). A total of 142,372 shotgun reads of 644-bp average length was generated. In addition, an 8-kb-insert paired-end sequencing run was performed based on the paired-end rapid library preparation protocol for Titanium chemistry (Roche, March 2012), with modifications as described previously (Hill et al., Protocol Exchange (2014) doi:10.1038/protex.2014.028). A total of 170,435 paired-end reads was generated, with an estimated pair distance of 6,383±1,595 bp. Assembly of all sequencing runs together produced an improved high-quality draft sequence, with 35× genome coverage. The data were assembled using Newbler version 3.0 (454 Life Sciences), generating 3 scaffolds of 4,253,622 bp (containing 19 contigs; SEQ ID NO:19 to SEQ ID NO:37, Table 4), 258,581 bp (1 contig; SEQ ID NO:38), and 4,841 bp (1 contig; SEQ ID NO:39), respectively. The sequence data were annotated using the Prokaryotic Genome Annotation Pipeline version 3.1 (NCBI).

TABLE 4

| Contig | Location in scaffold | Number of base pairs | Sequence |
|---|---|---|---|
| 1 | 1 to 20368 | 20368 | SEQ ID NO: 19 |
| 2 | 20493 to 46135 | 25643 | SEQ ID NO: 20 |
| 3 | 46208 to 66053 | 19846 | SEQ ID NO: 21 |
| 4 | 66079 to 256125 | 190047 | SEQ ID NO: 22 |
| 5 | 256156 to 582121 | 325966 | SEQ ID NO: 23 |
| 6 | 582147 to 998882 | 416736 | SEQ ID NO: 24 |
| 7 | 1003835 to 1191389 | 187555 | SEQ ID NO: 25 |
| 8 | 1191475 to 1272502 | 81028 | SEQ ID NO: 26 |
| 9 | 1272530 to 1482163 | 209634 | SEQ ID NO: 27 |
| 10 | 1482225 to 1573044 | 90820 | SEQ ID NO: 28 |
| 11 | 1573080 to 1697136 | 124057 | SEQ ID NO: 29 |
| 12 | 1698282 to 1776987 | 78706 | SEQ ID NO: 30 |
| 13 | 1777265 to 2007632 | 230368 | SEQ ID NO: 31 |
| 14 | 2007658 to 2156687 | 149030 | SEQ ID NO: 32 |
| 15 | 2156715 to 2486251 | 329537 | SEQ ID NO: 33 |
| 16 | 2486290 to 2527990 | 41701 | SEQ ID NO: 34 |
| 17 | 2528079 to 3060107 | 532029 | SEQ ID NO: 35 |
| 18 | 3060133 to 3413802 | 353670 | SEQ ID NO: 36 |
| 19 | 3413828 to 4253622 | 839795 | SEQ ID NO: 37 |

*Arthrobacter* sp. strain OY3WO11 has a total genome size of 4,517,044 bp, with a G+C content of 65.29%. Genome annotation reveals 4,225 genes and 4,163 protein-coding genes. The genome features 1 gene encoding 5S rRNA, 2 genes encoding 16S rRNA, 1 gene encoding 23S rRNA, and 50 tRNA-encoding genes.

The genome of *Arthrobacter* sp. strain OY3WO11 contains genes that have been associated with biocontrol phenotypes, including phenazine carboxylic acid synthesis and cell wall-degradative enzymes. Two genes encoding putative beta-lactamases were observed. The sequences of taxonomic markers, including the 16S rRNA-encoding gene and rpoB, share 97 to 99% identity with the corresponding genes found in *Arthrobacter phenanthrenivorans* Sphe3. Similarly, two copies of the bacterial barcode marker cpn60 were identified, each of which clustered with corresponding copies from *Arthrobacter phenanthrenivorans* Sphe3 by phylogenetic analysis and have sequence identities of 93 to 96%. Comparison of the genome sequence of *Arthrobacter* sp. strain OY3WO11 to 85 genomic sequences from *Arthrobacter* spp. annotated at the Integrated Microbial Genomes portal revealed that the average nucleotide identity (ANI) of the genome of strain OY3WO11 was below the specified cutoff for inclusion in any of the species included in the analysis (the closest ANI was *Arthrobacter phenanthrenivorans* Sphe3, at 85.25%). In addition, SpecI (Mende et al., Nat Methods (2013), 10: 881-884) could not assign strain OY3WO11 to a species cluster; the closest match was *Arthrobacter phenanthrenivorans* Sphe3, with an average ANI of 93.9% over 40 Clusters of Orthologous Groups (COGs). Taken together, these observations suggest that strain OY3WO11 may represent a previously uncharacterized or unsequenced strain of *Arthrobacter*. This whole-genome shotgun project has been deposited at DDBJ/ENA/GenBank under the accession nos. LWLP00000000 and LWLP01000000 (Town et al., *Genome Announcements* (May/June 2016) 4(3): e00585-16).

*Bacillus subtilis* Strain WAUSV36

Genomic DNA was purified from 1 mL of an overnight culture in YGM (Example 1) of *Bacillus subtilis* strain WAUSV36 using a Wizard genomic DNA (gDNA) extraction kit (Promega, Madison, Wis., USA) and sequenced on the GS Junior using the paired-end rapid library preparation protocol for Titanium chemistry (Roche, March 2012), with modifications as described previously (Hill et al., Protocol Exchange (2014) doi:10.1038/protex.2014.028). Reads from two paired-end sequencing runs (average read lengths of 418 and 419 bp) were assembled using Newbler version 3.0 (454 Life Sciences). The total number of filter-passed reads was 309,047. These reads were assembled into 2 scaffolds of 4,179,279 bp (19 contigs; SEQ ID NO:40 to SEQ ID NO:58, Table 5) and 59,592 bp (1 contig; SEQ ID NO:59), respectively. The $N_{50}$ contig size was 1,049,070 bp. Assembly of all sequencing data produced an improved high-quality draft sequence featuring 25× genome coverage. Sequence data were annotated using the Prokaryotic Genome Annotation Pipeline version 3.1 (NCBI).

TABLE 5

| Contig | Location in scaffold | Number of base pairs | Sequence |
|---|---|---|---|
| 1 | 1 to 55345 | 55345 | SEQ ID NO: 40 |
| 2 | 55436 to 58401 | 2966 | SEQ ID NO: 41 |
| 3 | 58427 to 59953 | 1527 | SEQ ID NO: 42 |
| 4 | 59979 to 75421 | 15443 | SEQ ID NO: 43 |
| 5 | 75447 to 78412 | 2966 | SEQ ID NO: 44 |
| 6 | 78829 to 80355 | 1527 | SEQ ID NO: 45 |
| 7 | 80474 to 1129543 | 1049070 | SEQ ID NO: 46 |
| 8 | 1130965 to 1133929 | 2965 | SEQ ID NO: 47 |
| 9 | 1134574 to 1341361 | 206788 | SEQ ID NO: 48 |
| 10 | 1341387 to 1487681 | 146295 | SEQ ID NO: 49 |
| 11 | 1487707 to 1537269 | 49563 | SEQ ID NO: 50 |
| 12 | 1537295 to 1915605 | 378311 | SEQ ID NO: 51 |
| 13 | 1915842 to 2014432 | 98591 | SEQ ID NO: 52 |
| 14 | 2014495 to 2177840 | 163346 | SEQ ID NO: 53 |
| 15 | 2177866 to 3402322 | 1224457 | SEQ ID NO: 54 |
| 16 | 3402456 to 3405421 | 2966 | SEQ ID NO: 55 |
| 17 | 3407164 to 3715576 | 308413 | SEQ ID NO: 56 |
| 18 | 3715749 to 3718714 | 2966 | SEQ ID NO: 57 |
| 19 | 3720140 to 4179279 | 459140 | SEQ ID NO: 58 |

The genome size of *Bacillus subtilis* strain WAUSV36 is 4,238,871 bp and is composed of 43.32% G+C content. A total of 4,510 genes and 4,404 protein-coding genes were observed, along with 2 genes encoding 5S rRNA, 3 genes encoding 16S rRNA, 5 genes encoding 23S rRNA, and 60 tRNA-encoding genes. A total of 1,688 Clusters of Orthologous Group (COG) clusters were identified by annotation using the Integrated Microbial Genomes (IMG) portal.

The sequences of taxonomic markers, such as the 16S rRNA-encoding gene and rpoB, are >99% identical to the corresponding sequences of many strains of *Bacillus subtilis*. Similarly, the single-copy bacterial barcode marker cpn60 is identical in sequence to several strains of *Bacillus subtilis*. At the whole-genome level, strain WAUSV36 has pairwise average nucleotide identities of 99.96% with 25 strains of *Bacillus subtilis* available at the IMG portal and is below the specified nucleotide identity cutoff for other species of *Bacillus*. Finally, SpecI (Mende et al., Nat Methods (2013), 10: 881-884) assigned strain WAUSV36 to the species cluster *Bacillus subtilis*, with an average of 98.93% identity over 40 COGs. These observations suggest that strain WAUSV36 is a strain of *Bacillus subtilis*.

Similar to other strains of *Bacillus subtilis* associated with biocontrol phenotypes, the genome of strain WAUSV36 featured genes involved in biofilm formation, but no genes associated with surfactin production were observed. Five genes encoding putative beta-lactamases and three cellulase genes were also found. This whole-genome shotgun project has been deposited at DDBJ/ENA/GenBank under the accession nos. LWLQ00000000 and LWLQ01000000 (Town et al., *Genome Announcements* (May/June 2016) 4(3): e00586-16).

Example 6

Determination of Antifungal Activity by Measuring Fungal Growth Using an Indirect Impedance Assay The method used for evaluating antifungal activities of bacterial isolates against *Phytophthora infestans* is similar to that described by He, J. et al. "Concurrent selection for microbial suppression of *Fusarium graminearum*, fusarium head blight and deoxynivalenol in wheat" *Journal of Applied Microbiology* (2009), 106(6), 1805-1817. Growth of *Phytophthora infestans* in liquid medium in the presence or absence of cell-free culture filtrates of the bacterial isolates to be tested is measured by a Microbiological Impedance Analyser (BacTrac™ 4300, Sy-Lab Instruments GmbH, Austria). Microbial growth is measured based on reduction of impedance of the medium caused by the production of small, charged compounds as microbial growth proceeds.

Cell-Free Bacterial Culture Filtrates:

Bacterial isolates (OY3WO11, 189, WAUSV36, KENGFT3, OXWO6B1 and UWO1) stored at −80° C. are suspended in potato dextrose broth (PDB (Difco™), Becton, Dickinson and Company) or minimal medium (M M, Shao, S., Zhou, T., and McGarvey, B. D. "Comparative metabolomic analysis of *Saccharomyces cerevisiae* during the degradation of patulin using gas chromatography-mass spectrometry.", *Applied Microbiology and Biotechnology*, (2012) 94(3), pp. 789-797), and adjusted to an optical density (OD) reading of 1.0 (620 μm). Medium (PDB or MM; 24 mL) in a 50 mL Falcon™ tube is inoculated with 1 mL of the bacterial suspension. The inoculated tubes are incubated at room temperature (23±2° C.) on a rotary shaker at 150 rpm for 6 days. The resulting bacterial cultures are centrifuged at 2,650 g for 10 min and the supernatants are filtered through a 0.22 μm syringe filter (mixed cellulose ester; MCE) into fresh tubes, to provide cell-free bacterial culture filtrates.

Assay Conditions:

For each experiment, five samples (discs 9 mm in diameter) cut from *Phytophthora infestans* cultures grown on Rye B agar (Caten, C. E. and J. L. Jinks. "Spontaneous variability of single isolates of *Phytophthora infestans*. I. Cultural variation." *Can. J. Bot.* (1968) 46: 329-348) for 2-3 weeks are each placed into a measuring tube of the Microbiological Impedance Analyser, followed by addition of 2 mL of cell-free bacterial culture filtrate. Sterile medium is used as a control. Fungal growth (measured by impedance changes) is monitored at 20 min intervals for 120 h at 22° C. Each experiment is replicated three times.

Data Analysis:

Curves of impedance changes are analyzed using the BacEval™ computer program (Sy-lab Instruments GmbH (2002): BacTrac™ 4000 Series Microbiological Operation Manual V1.05e). Data of impedance measurements is transformed inversely and used as indicator of fungal growth. The data are statistically analyzed using SAS/STAT™ 9.2 (SAS), general linear model (GLM) procedures. Fungal growth curves were compared using CONTRASTS (SAS); means of fungal growth at each time point are compared using Tukey's test.

Results

Statistical analysis for all 6 bacterial isolates indicated that growth curves of *Phytophthora infestans* in the two media used, MM and PDB, are significantly different (P<0.001), and were analysed separately.

Figure 6:
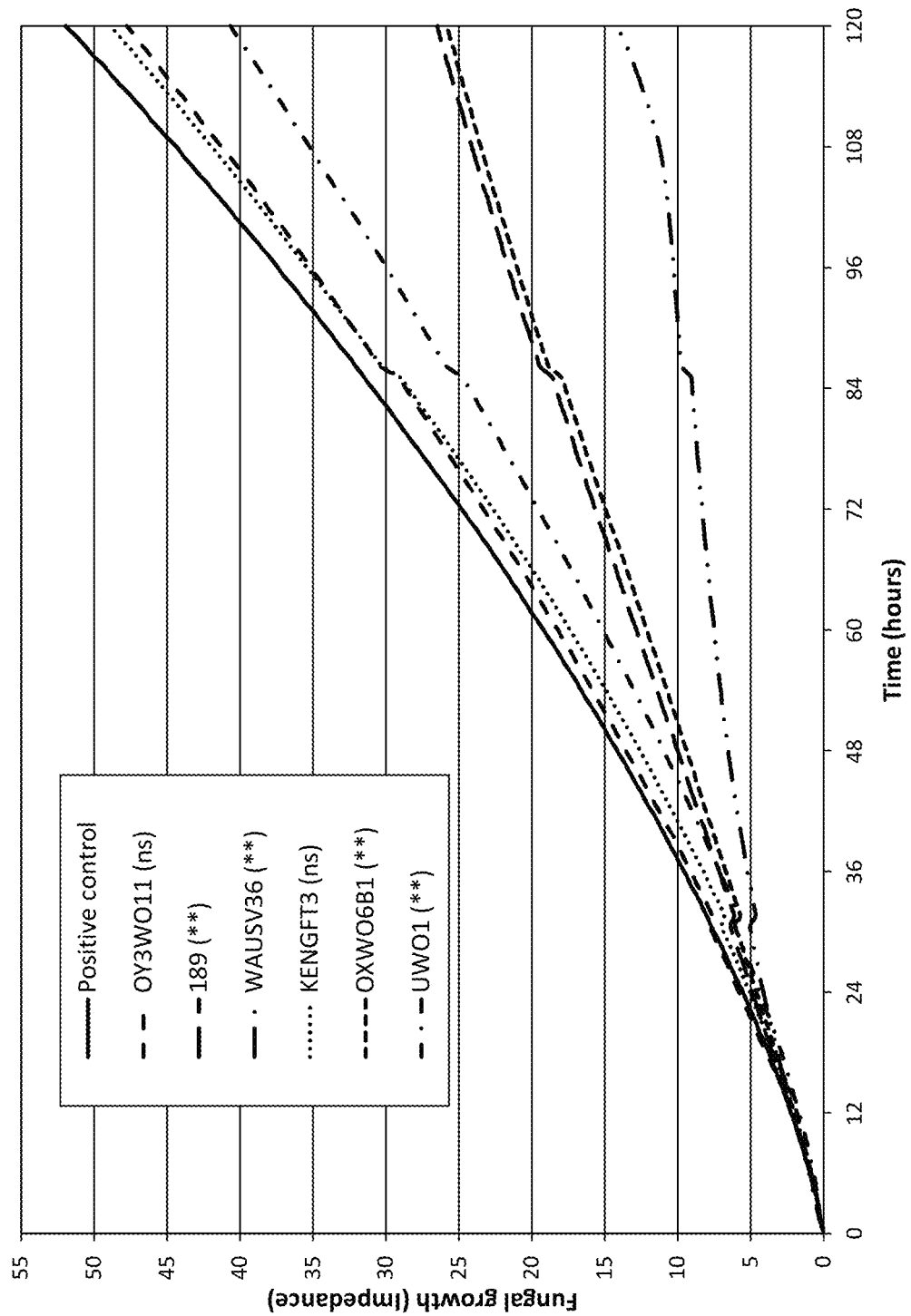
FIG. 6 is a graph showing the growth of *Phytophthora infestans* in minimal medium (MM) in the presence of cell-free bacterial culture filtrates or sterile medium (positive control), as determined by impedance measurements. "ns" indicates not significantly different from the control at the $p=0.05$ level; "**" indicates significantly different from the control at the $p=0.01$ level.

As seen in FIG. 6, growth of *Phytophthora infestans* was fastest in MM in the absence of cell-free bacterial culture filtrates (positive control). Among the 6 bacteria tested, cell-free filtrates from 4 bacterial strains (189, WAUSV36, OXWO6B1 and UWO1) showed significant inhibition of fungal growth (P<0.01). However, growth of *Phytophthora infestans* treated with cell-free filtrates from bacterial isolates OY3WO11 and KENGFT3 was not statistically significantly different from that of the control (P>0.05).

Figure 7:
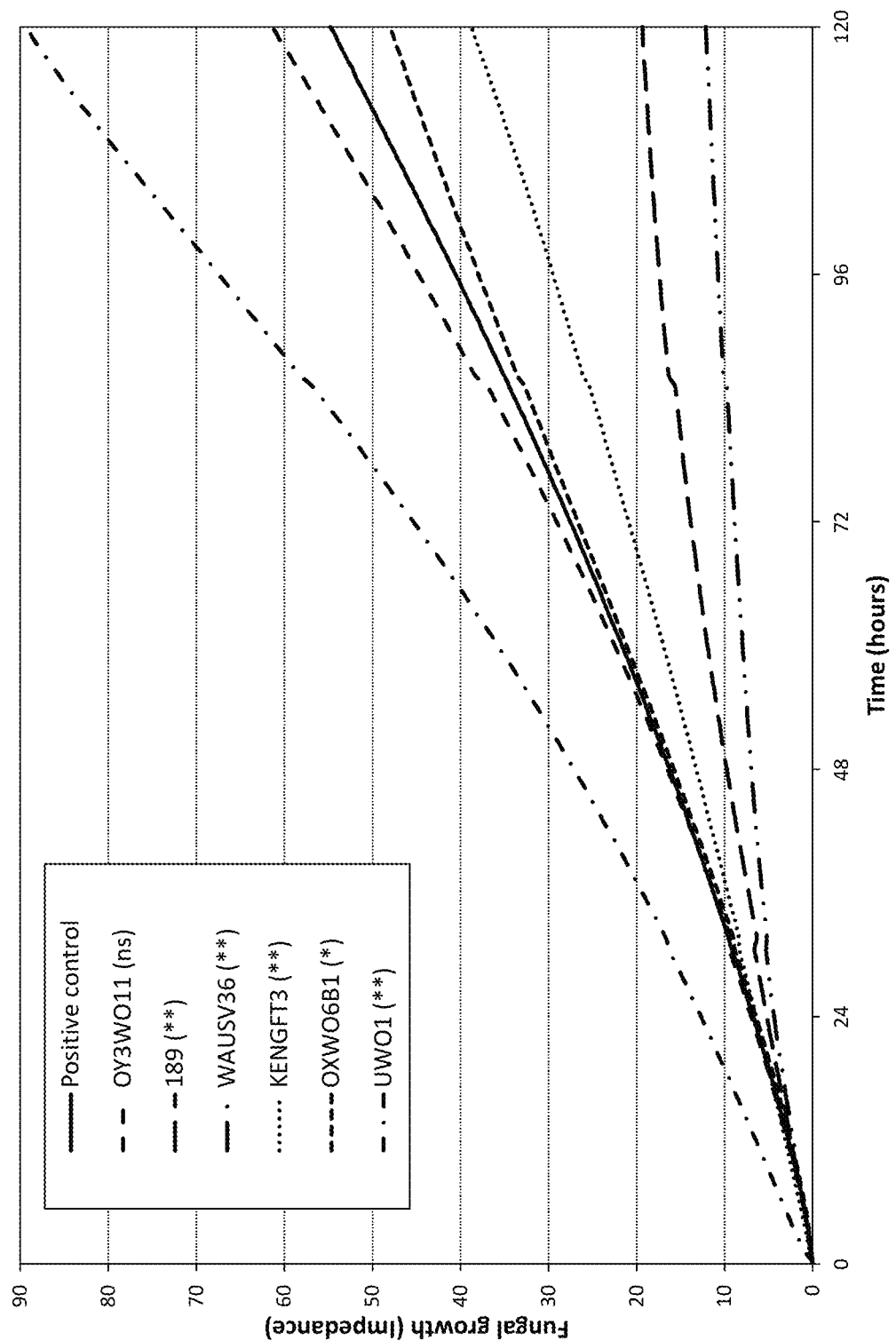
FIG. 7 is a graph showing the growth of *Phytophthora infestans* in potato dextrose broth (PDB) in the presence of cell-free bacterial culture filtrates or sterile medium (positive control), as determined by impedance measurements. "ns" indicates not significantly different from the control at the $p=0.05$ level; "*" indicates significantly different from the control at $p=0.05$ level and "**" indicates significantly different from the control at $p=0.01$ level.

As seen in FIG. 7, four cell-free bacterial culture filtrates (from strains 189, WAUSV36, OXWO6B1 and KENGFT3) inhibited growth of *Phytophthora infestans* in PDB. The cell-free filtrate from isolate OXWO6B1 showed statistically significant growth inhibition (p=0.05), and the cell-free filtrates from isolates WAUSV36, 189 and KENGFT3 showed even stronger growth inhibition (p=0.01). The cell-free filtrate from isolate OY3WO11 showed no significant effect on the growth of the pathogen, and the cell-free filtrate from isolate UWO1 significantly stimulated growth of *Phytophthora infestans* (p=0.01).

Figure 8:
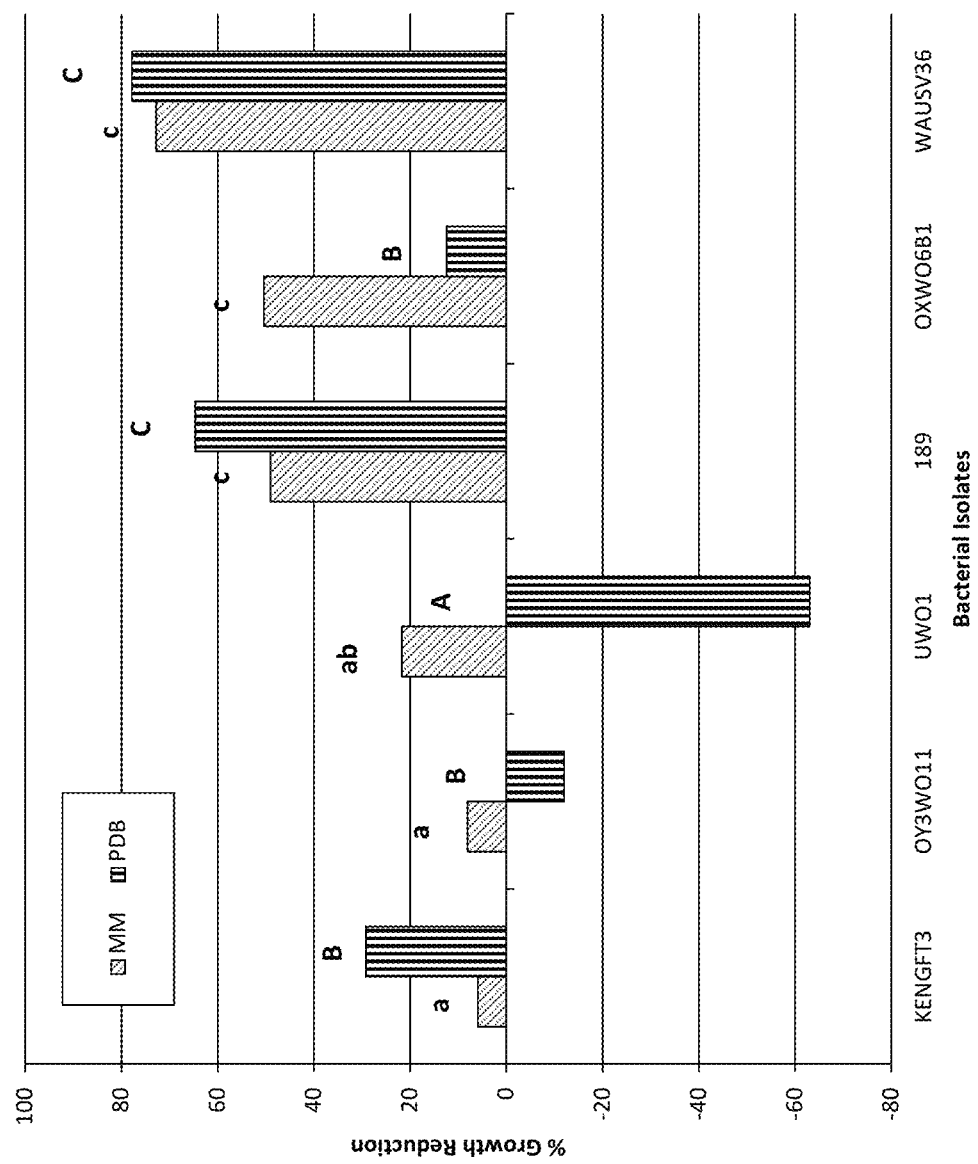
FIG. 8 is a bar graph showing percent growth reduction of *Phytophthora infestans* at 120 hours in the presence of cell-free bacterial culture filtrates compared with growth in the presence of sterile medium (positive control) as determined by impedance measurements. Means indicated with the same letter (A/a, B/b or C/c, for PDB and MM media, respectively) are not significantly different according to Tukey's test (Tukey, J. "Comparing Individual Means in the Analysis of Variance". *Biometrics* (1949) 5(2): 99-114) at the p=0.05 level.

FIG. 8 shows the percent growth inhibition of *Phytophthora infestans* after 120 hours incubation in the presence of cell-free bacterial culture filtrates compared to growth in the presence of sterile medium (positive control). Means indicated with the same letter (A/a, B/b or C/c, for PDB and MM media, respectively) are not significantly different according to Tukey's test (Tukey, J. "Comparing Individual Means in the Analysis of Variance". *Biometrics* (1949) 5 (2): 99-114) at the p=0.05 level. In MM, cell-free filtrates from isolates WAUSV36, OXWO6B1 and 189 significantly reduced the fungal growth as compared with the control, and inhibited *Phytophthora infestans* growth by 72.8%, 50.4% and 49.0%, respectively. The cell-free filtrate from isolate UWO1 showed significantly weaker activity in MM, reducing *Phytophthora infestans* growth by 21.7%. In PDB, cell-free filtrates from isolates WAUSV36 and 189 inhibited the growth of *Phytophthora infestans* by 77.8% and 64.7%, respectively, compared to the control, significantly more than the cell-free filtrate from isolate KENGFT3, which reduced fungal growth by 29.2% in PDB.

The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples, but should be given the broadest interpretation consistent with the description as a whole.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10888096B2). An electronic copy of the "Sequence Listing" will also be available from the USPTO upon request and payment of the fee set forth in 37 CFR 1.19(b)(3).

The invention claimed is:

1. A method of controlling or treating potato late blight disease in plants, the method comprising:

formulating a bacterial culture into a biopesticidal formulation; and applying an effective amount of the biopesticidal formulation to a plant, or part thereof, infected by, or at risk of infection by, *Phytophthora infestans;* wherein the bacterial culture comprises an effective amount of one or more bacteria selected from the group consisting of:

*Pseudomonas chlororaphis* strain 189, International Depositary Authority of Canada accession number 151116-02;

*Bacillus subtilis* strain WAUSV36, International Depositary Authority of Canada accession number 151116-01;

*Pseudomonas fluorescens* strain UWO1, International Depositary Authority of Canada accession number 151116-03;

*Pseudomonas fluorescens* strain KENGFT3, International Depositary Authority of Canada accession number 151116-05;

*Arthrobacter* sp. strain OY3WO11, International Depositary Authority of Canada accession number 151116-04; and

*Pantoea* sp. strain OXWO6B1, International Depositary Authority of Canada accession number 151116-06.

2. The method of claim 1, wherein the bacterial culture comprises *Pseudomonas chlororaphis* strain 189, International Depositary Authority of Canada accession number 151116-02.

3. The method of claim 1 wherein the plant is a solanaceous crop.

4. The method of claim 1 wherein the plant is potato.

5. The method of claim 1 wherein the plant is tomato.

6. The method of claim 1 wherein the biopesticidal formulation is applied by spraying.

7. The method of claim 1 wherein the biopesticidal formulation is applied to plants growing in a field.

8. The method of claim 1 wherein the biopesticidal formulation is applied to plants under cultivation in greenhouses or glasshouses.

9. The method of claim 1 wherein the biopesticidal formulation is applied to tubers prior to or during storage.

10. The method of claim 9 wherein the tubers are potato tubers.

11. The method of claim 1 wherein the biopesticidal formulation is applied to fruit before harvest.

12. The method of claim 11 wherein the fruit is tomato fruit.

13. A method of controlling or treating potato late blight disease in plants, the method comprising applying an effective amount of a biopesticidal formulation to a plant, or part thereof, infected by, or at risk of infection by, *Phytophthora infestans*, the biopesticidal formulation comprising a bacterial culture and a carrier, wherein the bacterial culture comprises an effective amount of one or more bacteria selected from the group consisting of:

*Pseudomonas chlororaphis* strain 189, International Depositary Authority of Canada accession number 151116-02;

*Bacillus subtilis* strain WAUSV36, International Depositary Authority of Canada accession number 151116-01;

*Pseudomonas fluorescens* strain UWO1, International Depositary Authority of Canada accession number 151116-03;

*Pseudomonas fluorescens* strain KENGFT3, International Depositary Authority of Canada accession number 151116-05;

*Arthrobacter* sp. strain OY3WO11, International Depositary Authority of Canada accession number 151116-04; and

*Pantoea sp.* strain OXWO6B1, International Depositary Authority of Canada accession number 151116-06.

14. The method of claim 13, wherein the biopesticidal formulation comprises *Pseudomonas chlororaphis* strain 189, International Depositary Authority of Canada accession number 151116-02.

15. The method of claim 13 wherein the plant is a solanaceous crop.

16. The method of claim 13 wherein the plant is potato.

17. The method of claim 13 wherein the plant is tomato.

18. The method of claim 13 wherein the biopesticidal formulation is applied by spraying.

19. The method of claim 13 wherein the biopesticidal formulation is applied to plants growing in a field.

20. The method of claim 13 wherein the biopesticidal formulation is applied to plants under cultivation in greenhouses or glasshouses.

21. The method of claim 13 wherein the biopesticidal formulation is applied to tubers prior to or during storage.

22. The method of claim 21 wherein the tubers are potato tubers.

23. The method of claim 13 wherein the biopesticidal formulation is applied to fruit before harvest.

24. The method of claim 23 wherein the fruit is tomato fruit.

* * * * *